United States Patent
Yamamoto

(10) Patent No.: US 6,777,563 B2
(45) Date of Patent: Aug. 17, 2004

(54) 3-FLUOROALKOXYMETHYL-3-ALKYLOXETANES

(75) Inventor: Akinori Yamamoto, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/713,051

(22) Filed: Nov. 17, 2003

(65) Prior Publication Data

US 2004/0097744 A1 May 20, 2004

Related U.S. Application Data

(62) Division of application No. 10/221,191, filed as application No. PCT/JP01/01940 on Mar. 13, 2001, now Pat. No. 6,673,947.

(30) Foreign Application Priority Data

Mar. 31, 2000 (JP) .......................................... 2000-96920

(51) Int. Cl.$^7$ ............................................ C07D 305/06
(52) U.S. Cl. ........................ 549/511; 549/510; 549/511
(58) Field of Search .................................. 549/511, 510

(56) References Cited

U.S. PATENT DOCUMENTS 5,650,483 A  7/1997 Malik et al. ................. 528/402

FOREIGN PATENT DOCUMENTS

| GB | 2269816 A |   | 2/1994 |            |
|----|-----------|---|--------|------------|
| GB | 2269816 A | * | 2/1994 | C07D/306/08 |
| JP | 2000-191652 |   | 7/2000 |          |

OTHER PUBLICATIONS

JP Database 13:106364; Patent No. 2000191652—Fluorine-containing . . . compositions, and manufacture thereof; Jul. 11, 2000.

* cited by examiner

Primary Examiner—Joseph K. McKane
Assistant Examiner—Janet L Coppins
(74) Attorney, Agent, or Firm—Armstrong, Kratz, Quintos, Hanson & Brooks, LLP

(57) ABSTRACT

The present invention provides a process for synthesizing 3-fluoroalkoxymethyl-3-alkyloxetanes, suitable as intermediates for preparing various fluorine-containing functional materials, represented by General Formula (Ia):

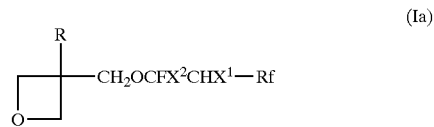

wherein, $X^1$ and $X^2$ independently represent hydrogen or fluorine; Rf represents fluorine or $C_1$–$C_{18}$ linear or branched perfluoroalkyl; and R represents methyl, ethyl, n-propyl or isopropyl.

1 Claim, No Drawings

3-FLUOROALKOXYMETHYL-3-ALKYLOXETANES

CROSS REFERENCE TO RELATED APPLICATION

This application is a division of U.S. Ser. No. 10/221,191, filed Sep. 23, 2002 now U.S. Pat. No. 6,673,947, which is a 35 U.S.C. 371 application of international application No. PCT/JP01/01940 filed Mar. 13, 2001, which is based on Japanese Application No. 2000-96920 filed Mar. 31, 2000.

TECHNICAL FIELD

The present invention relates to a process for preparing 3-fluoroalkoxymethyl-3-alkyloxetanes or mixtures thereof useful as intermediates for preparing various fluorine-containing functional materials.

BACKGROUND OF THE INVENTION

In a known method for synthesizing 3-fluoroalkoxymethyl-3-alkyloxetanes, for example, 3-bromomethyl-3-methyloxetane is condensed using a fluoroalkyl alcohol and an alkali (Japanese Unexamined Patent Publication No. 500422/1999). However, this method requires the use of expensive 3-bromomethyl-3-methyloxetane. In addition, some of the desired compounds cannot be produced by the method because of its limitation due to the reaction mechanism.

DISCLOSURE OF THE INVENTION

The present invention provides 3-fluoroalkoxymethyl-3-alkyloxetanes and a production process therefor. Particularly, the invention provides compounds having a fluoroalkyl ether bond where such an exocyclic ether bond has a difluoromethylene or fluoromethylene group at the α-position, and a production process therefor.

The present inventors found that addition of 3-alkyloxetane methanol as a starting compound to a fluoroolefin in the presence of an alkali can produce desired 3-fluoroalkoxymethyl-3-alkyloxetanes or mixtures thereof. It is important to maintain the reaction system under an alkali condition because the oxetane ring cleaves under an acidic condition.

Further, according to the instant process, 3-(1,1,2,3,3,3-hexafluoropropoxy)methyl-3-methyloxetane can be synthesized, which cannot be produced through conventional processes. Some desired compounds cannot be synthesized by conventional processes because of the instability of the corresponding fluoroalcohols employed in the reaction.

The features of the invention are shown in the following Items 1 to 6.

Item 1. A process for preparing a 3-fluoroalkoxymethyl-3-alkyloxetane represented by General Formula (I) or a mixture thereof, the process comprising adding a 3-alkyloxetane methanol (1) to at least one of fluoroolefins (2) under an alkali condition:

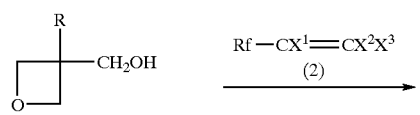

(1)

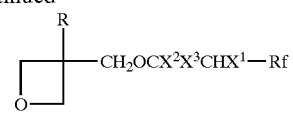

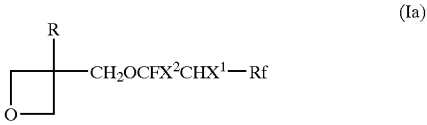

(I)

wherein, $X^1$, $X^2$ and $X^3$ independently represent hydrogen or fluorine; Rf represents fluorine or $C_1$–$C_{18}$ linear or branched perfluoroalkyl; and R represents methyl, ethyl, n-propyl or isopropyl.

Item 2. A process according to Item 1 wherein the reaction is conducted in a two-phase system composed of an organic solvent and an alkali aqueous solution in the presence of a phase transfer catalyst.

Item 3. A process according to Item 1 wherein R represents methyl.

Item 4. A process according to Item 1 wherein Rf represents trifluoromethyl; and $X^1$, $X^2$ and $X^3$ represent fluorine.

Item 5. A process according to Item 1 for preparing 3-(1,1,2,3,3,3-hexafluoropropoxy)methyl-3-methyloxetane wherein R represents methyl; Rf represents trifluoromethyl; and $X^1$, $X^2$ and $X^3$ represent fluorine.

Item 6. A compound represented by General Formula (Ia)

$$\underset{O}{\overset{R}{\rule{0pt}{0pt}}}\!\!\!\!\!\!\!\!\!\!\!\!\!\text{—CH}_2\text{OCFX}^2\text{CHX}^1\text{—Rf}$$

(Ia)

wherein, $X^1$ and $X^2$ independently represent hydrogen or fluorine; Rf represents fluorine or $C_1$–$C_{18}$ linear or branched perfluoroalkyl; and R represents methyl, ethyl, n-propyl or isopropyl.

3-alkyloxetane methanol (1) and fluoroolefin (2) employed as starting compounds herein are both known compounds.

The reaction of the invention is conducted in a liquid phase using a solvent and a base at temperatures ranging from the ice-cooled temperature to the reflux temperature of the solvent, usually at room temperature, for 1 to 6 hours. The reaction is preferably conducted in a pressure-tight vessel when the boiling point of the fluoroolefin to be reacted is lower than the reaction temperature. From about 1 mole to about an excess amount of a fluoroolefin (2) and from about 1 mole to about an excess amount of a base are used per mole of 3-alkyloxetane methanol. Preferable solvents include aliphatic hydrocarbons such as hexane, heptane and the like; alicyclic hydrocarbons such as cyclohexane and the like; aromatic hydrocarbons such as benzene, toluene, xylene and the like; halogenated hydrocarbons such as chloroform, dichloromethane, carbon tetrachloride, perfluorohexane and the like; ethers such as tetrahydrofuran and the like; ketones such as acetone, methyl ethyl ketone and the like; organic solvents such as acetonitrile, DMF, DMSO and the like; and water. Preferable bases include alkali metal hydroxides such as sodium hydroxide, potassium hydroxide, lithium hydroxide and the like; alkali earth metal hydroxides such as calcium hydroxide, magnesium hydroxide and the like; and alkali metal carbonates or alkali metal hydrogencarbonates such as sodium carbonate, potassium carbonate, sodium hydrogencarbonate, potassium hydrogencarbonate and the like. These bases are preferably added to the reaction system in the form of an aqueous solution.

R represents methyl, ethyl, n-propyl or isopropyl, preferably methyl or ethyl, more preferably methyl.

Rf represents fluoroalkyl, preferably $C_1$–$C_{18}$ linear or branched perfluoroalkyl such as $(CF_2)_nCF_3$ (n represents an integer from 0 to 17), perfluoroisopropyl, perfluoroisobutyl or perfluoro-t-butyl, more preferably $C_2$–$C_{18}$ perfluoroalkyl.

$X^1$, $X^2$ and $X^3$ independently represent hydrogen or fluorine; preferably when $X^1$ represents hydrogen or fluorine, both $X^2$ and $X^3$ represent fluorine, or either $X^2$ or $X^3$ represents hydrogen and the other represents fluorine; most preferably $X^1$, $X^2$ and $X^3$ represent fluorine.

The production process according to the invention is preferably conducted in the presence of a phase transfer catalyst to increase the reaction rate. Preferable phase transfer catalysts include tetrabutylammonium chlorinate and the like. The phase transfer catalyst can be used in amounts from a catalytic amount to about 1 mole per mole of 3-alkyloxetane methanol.

After the reaction, unreacted 3-alkyloxetane methanol is dissolved in the alkaline aqueous phase and is not extracted with ordinary organic solvents. Therefore, the desired product is recovered by the extraction in a substantially pure state.

The starting compound 3-alkyloxetane methanol is obtainable, for example, from the cyclization of alkyltrihydroxymethyl methane.

According to the invention, 3-fluoroalkoxymethyl-3-alkyloxetanes can easily be produced. Specifically, novel oxetane derivatives having $CF_2$ or CFH at the α-position of ether can easily be obtained.

3-fluoroalkoxymethyl-3-alkyloxetanes produced by the invention are useful as intermediates for preparing various fluorine-containing functional materials such as a surface modifier for resins, coatings, etc.

BEST MODE FOR CARRYING OUT THE INVENTION

Examples are given below to illustrate the invention in more detail, but it is to be understood that the invention is not limited thereto.

EXAMPLE 1

3-methyl-3-oxetane methanol (6.3 g), tetrabutylammonium chloride (0.8 g), hexane (90 ml) and 50% aqueous sodium hydroxide solution (81 g) were placed into a 1L autoclave. After the autoclave was evacuated, hexafluoropropene (28 g) was introduced therein. Four minutes after the introduction, the reaction temperature increased from 28.4° C. to 33.7° C. and the pressure decreased from 1.7 kg/cm²G to 0.4 kg/cm²G Further stirred for 1 hour, the reaction solution was taken out; the aqueous phase and the hexane phase were separated; and extraction was conducted on the aqueous phase using methylene chloride. The methylene chloride phase was combined with the organic phase and washed with water. The product obtained was analyzed by gas chromatography to show that the starting compound 3-methyl-3-oxetane methanol had disappeared and only the desired 3-(1,1,2,3,3,3-hexafluoropropoxy)methyl-3-methyloxetane was detected. After isolation, 14.2 g of the product was obtained in an yield of 93%. The structure of the product was identified by hydrogen NMR and fluorine NMR.

$^1$H-NMR (CDCl$_3$:δ(ppm)) 1.37(s,3H), 4.13(s,1H), 4.42 (d,2H), 4.48(d,2H)

$^{19}$F-NMR (−67.8 ppm(1F), −75.7(3F), −80.3(1F), −83.6 (1F))

EXAMPLE 2

3-methyl-3-oxetane methanol (6.3 g), tetrabutylammonium chloride (0.8 g), hexane (90 ml) and 50% aqueous sodium hydroxide solution (81 g) were placed into a 1L autoclave. After the autoclave was evacuated, octafluoro-1-butene (37 g) was introduced therein. Six minutes after the introduction, the reaction temperature increased from 27° C. to 30° C. Further stirred for 1 hour, the reaction solution was taken out; the aqueous phase and the hexane phase were separated; and extraction was conducted on the aqueous phase using methylene chloride. The methylene chloride phase was combined with the organic phase was washed with water. The product obtained was analyzed by gas chromatography to show that the starting compound 3-methyl-3-oxetane methanol had disappeared and only the desired 3-methyl-3-(1,1,2,3,3,4,4,4-octafluorobutoxy) methyloxetane was detected. After isolation, 17.3 g of the product was obtained in an yield of 95%.

EXAMPLE 3

3-methyl-3-oxetane methanol (6.3 g), hexane (90 ml) and 50% aqueous sodium hydroxide solution (81 g) were placed into a 1L autoclave. After the autoclave was evacuated, hexafluoropropene (28 g) was introduced therein. Although no temperature increase was observed after the introduction, the pressure decreased from 1.6 kg/cm²G to 0.8 kg/cm²G Further, stirred for 1 hour, the reaction solution was then taken out; the aqueous phase and the hexane phase were separated; and extraction was conducted on the aqueous phase using methylene chloride. The methylene chloride phase was combined with the organic phase and washed with water. The product obtained was analyzed by gas chromatography resulting to show that the starting compound 3-methyl-3-oxetane methanol had disappeared and only the desired 3-(1,1,2,3,3,3-hexafluoropropoxy)methyl-3-methyloxetane was detected. After isolation, 6.8 g of the product was obtained in a yield of 44%.

INDUSTRIAL APPLICABILITY

Using 3-alkyloxetane methanol as a starting compound and adding this compound to a fluoroolefin in the presence of an alkali, the present invention provides a process for synthesizing 3-fluoroalkoxymethyl-3-alkyloxetanes suitable as intermediates for preparing various fluorine-containing functional materials.

What is claimed is:

1. A compound represented by General Formula (Ia)

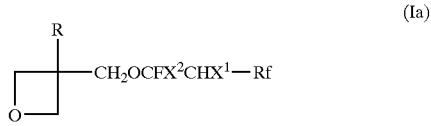

(Ia)

wherein, $X^1$ and $X^2$ independently represent hydrogen or fluorine; Rf represents fluorine or $C_1$–$C_{18}$ linear or branched perfluoroalkyl; and R represents methyl, ethyl, n-propyl or isopropyl.

* * * * *

UNITED STATES PATENT AND TRADEMARK OFFICE
CERTIFICATE OF CORRECTION

PATENT NO. : 6,777,563 B2  
APPLICATION NO. : 10/713051  
DATED : August 17, 2004  
INVENTOR(S) : Akinori Yamamoto Page 1 of 1

It is certified that error appears in the above-identified patent and that said Letters Patent is hereby corrected as shown below:

On the Title page:

Item "(54)" and Col. 1, lines 1-2  
"3-FLUOROALKOXYMETHYL-3-ALKYLOXETANES"

Should read:

Item "(54)" --PROCESS FOR PREPARING 3-FLUOROALKOXYMETHYL-3-ALKYLOXETANES--

Signed and Sealed this

Twentieth Day of January, 2009

JON W. DUDAS  
*Director of the United States Patent and Trademark Office*